(12) United States Patent
Ellis

(10) Patent No.: US 6,268,383 B1
(45) Date of Patent: Jul. 31, 2001

(54) SUBSTITUTED AROMATIC COMPOUNDS FOR TREATMENT OF ANTIBIOTIC-RESISTANT INFECTIONS

(75) Inventor: William Y. Ellis, Laurel, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/275,878

(22) Filed: Mar. 25, 1999

Related U.S. Application Data
(60) Provisional application No. 60/079,383, filed on Mar. 26, 1998.

(51) Int. Cl.$^7$ .................................................. A01N 43/40
(52) U.S. Cl. .......................... 514/325; 546/203; 548/528; 514/428; 514/653
(58) Field of Search ..................... 546/203, 115; 514/325, 653, 302

(56) References Cited

U.S. PATENT DOCUMENTS
4,818,767 * 4/1989 Rossignol ........................... 564/355

* cited by examiner

*Primary Examiner*—Bernard Dentz
(74) *Attorney, Agent, or Firm*—Elizabeth Arwine; Charles H. Harris

(57) ABSTRACT

This invention relates to compounds of the general formula:

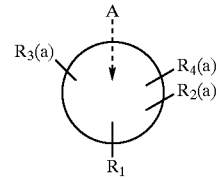

wherein A is a aromatic hydrocarbon ring system and $R_1$ is a carbon bound directly to an oxygen and is also bound to a nitrogen through a saturated carbon and wherein at least one of $R_2$, $R_3$ and $R_4$ is an electron-rich substituent.

The active agents are useful for treating patients suffering from infections including gram positive organisms, such as streptococcus, staphylococcus, anthracis, gram negative bacteria such as neisseria species, yeasts and mycobacterium. They are effective against strains which have shown resistance to other antimicrobial agents.

5 Claims, No Drawings

SUBSTITUTED AROMATIC COMPOUNDS FOR TREATMENT OF ANTIBIOTIC-RESISTANT INFECTIONS

This application takes priority from Provisional Application 60/079,383 filed Mar. 26, 1998.

FIELD OF THE INVENTION

This invention relates to the treatment of antibiotic-resistant infections, including particularly infections caused by bacteria, mycobacteria, fungi and yeasts. A preferred group of compositions of the invention contain as active agents compounds containing aryl ring systems, including phenyl, naphthyl and anthracene ring systems, substituted by a carbon bound to an oxygen which is also bound to a nitrogen through a saturated carbon or carbon chain which may be substituted with halo, hydroxy, alkoxy, amino or alkylamino are disclosed, In preferred embodiments, the aryl ring system is further substituted by at least two halo substituents or halo-substituted substituents.

BACKGROUND OF THE INVENTION

The benefit from use of antibiotics as a means of treating infections has been increasingly compromised by the development of resistant strains of microorganisms. Most of the new drugs are derivatives of older compounds. It is necessary to develop new agents that will respond to the current needs for medicinals that will effectively control pathogenic microbial populations that are resistant to antibiotics.

Halofantrine is a known antimalarial having a phenanthrene ring system substituted by a carbon bound to an oxygen which is also bound to a nitrogen through a saturated $CH_2$—$CH_2$ chain to tertiary nitrogen having two butyl substituents. The phenanthrene ring system is further substituted with 2 chlorines and one trifluoromethyl.

SUMMARY OF THE INVENTION

This invention relates to compounds of the general formula:

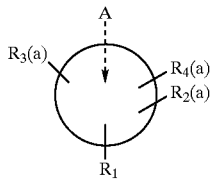

wherein A is a aromatic hydrocarbon ring system and $R_1$ is a carbon bound directly to an oxygen and is also bound to a nitrogen through a saturated carbon and wherein at least one of $R_2$, $R_3$ and $R_4$ is an electron-rich substituent.

The active agents are useful for treating patients suffering from infections including gram positive organisms, such as streptococcus, staphylococcus, anthracis, gram negative bacteria such as neisseria species, yeasts and mycobacterium. These compounds are effective against strains which have shown resistance to other antimicrobial agents.

DETAILED DESCRIPTION OF THE INVENTION

This invention relates to compounds that have use in treating several infectious diseases which are now resistant to treatment to conventionally used antibiotics. Some of the compounds described herein have had previously been suggested for use in treating malaria. Some of the compounds are newly discovered. Most of the compounds are lipophilic. The lipid solubility of these compounds should permit the drugs to enter into cells, including cells of the central nervous system. Many of the compounds could be also be absorbed from the intestinal tract when given orally. They may be administered as cyclodextrin inclusion complexes to increase bioavailability. They may also be administered transdermally. Using patches for transdermal administration makes it possible to more easily control dosage.

The active agents for use in accord with the teachings of this disclosure are of the general formula:

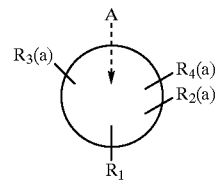

wherein A is an aromatic ring system and $R_1$ is bound directly to an oxygen and is also bound to a nitrogen through a saturated carbon. $R_1$ is of the structure CHOZX wherein Z may be hydrogen, a second bond to the oxygen, or may be carboxyl, ether or ester moiety wherein the ether or ester moiety may be alkyl of 1–8 carbons, phenyl, phenylalkyl, wherein the alkyl moiety consists of 1–4 carbons and wherein any said alkyl or phenyl group may, additionally, be substituted with hydroxy, alkyl of 1–2 carbons, alkenyl of 2–3 carbons, halo, amino, or alkyl amino group, X is $(CH_2)$ $N((CH2)_n(CH_3))_m$ wherein is 1–3, n is $\leq 6$, m is 1 or 2 with the proviso that when m is 2, at least one n is <3, or X may be $(CH_2)_o J$ wherein 0 is 0–4 and J is a saturated nitrogen-containing ring system with up to 10 carbon atoms in the ring system and may have up to 4 bridge carbons, wherein any saturated ring system may be substituted with alkyl, alkenyl, halo, alkoxy or haloalkyl moieties of 1–5 carbons or with phenyl, phenoxy, phenylalkyl, phenylalkoxy, carboxy or carbonyl groups, wherein the carboxy or carbonyl groups, including keto or ester moieties with alkyl groups of 1–4 carbons, alkenyl groups of 2–5 carbons or phenylalkyl wherein the alkyl is of 1–3 carbons or phenylalkoxy wherein the alkyl is of 1–3 carbons. Regarding substituents of $R_2(a)$, $R_3(a)$ and $R_4(a)$, a may be 0–4 with the proviso that at least one a is not 0. $R_2$, $R_3$ and $R_4$ may be alkyl (including cycloalkyl), a saturated, nitrogen-containing ring of 4–10 atoms, alkoxy, aryl, aryloxy, aryloxyalkyl, amino, aminoalkyl, alkyl-aminoalkyl, arylamino, alkenyl, arylalkenyl, arylalkylaminoalkyl, carboxyalkyl, hydroxy, halo, alkenyl, alkenyloxy, haloalkyl (including perhaloalkyl), wherein any alkyl has 1–8 carbons, alkenyl has 2–8 carbons, wherein halo is chloro, fluoro or bromo and aryl is a ring system of 1–3 rings with the provision that at least one of $R_2$, $R_3$ and $R_4$ is an electron-rich substituent. Z and X may be linked to form a heterocylic ring system. Furthermore, any alkyl or aryl at $R_2$, $R_3$ and $R_4$ may be further substituted with aryl of 1–2 rings, halo, (including multiple halo substitutions) alkyl, haloalkyl or alkoxy. Preferred halo substituents are chloro or bromo and a preferred haloalkyl is trifluoromethyl.

Compounds wherein X is $(CH_2)_o J$ and o is 2–4 are novel.

Particularly useful compounds are those of Formulas I, II, III and IV.

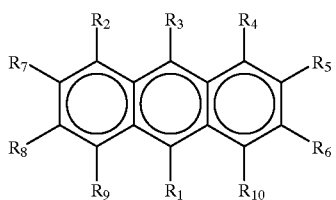

Formula I

In compounds of Formula I, any of $R_{2-8}$ may be substituents designated under $R_2$, $R_3$ and $R_4$ in the general formula above, with the proviso that at least one of $R_{2-8}$ is an electron-rich substituent and any one of $R_1$, $R_9$ or $R_{10}$ is a substituent as defined as $R_1$ in the general formula. Preferred compounds are those having at least two halos groups on the compound, with chloro or trifluoromethyl being particularly preferred groups.

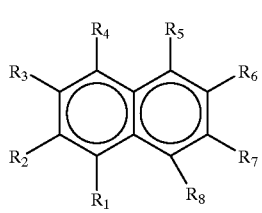

Formula II

In compounds of Formula II, any of $R_{2-6}$ may be substituents identified as $R_2$, $R_3$ or $R_4$ in the general formula with the proviso that at least one substituents is an electron-rich moiety and $R_1$ is as designated for $R_1$ (CHOZX) for the general formula above. Many of the preferred compounds have at least two halo or halo-substituted substituents.

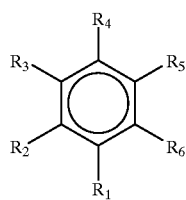

Formula III wherein $R_1$ is defined as in the general formula and $R_{2-6}$ is defined in the same manner as $R_2$, $R_3$ and $R_4$ in the general formula. May of the preferred compounds have least two halo or halo-substituted substituents.

A particularly valuable compound of Formula II is of the formula:

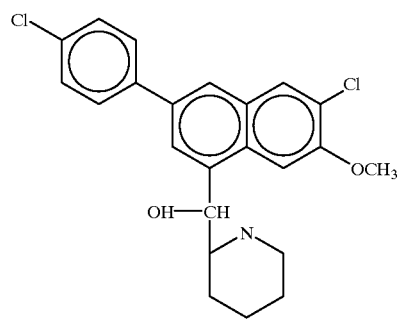

Compounds of Formulas I, II and III can be made using the following methods:

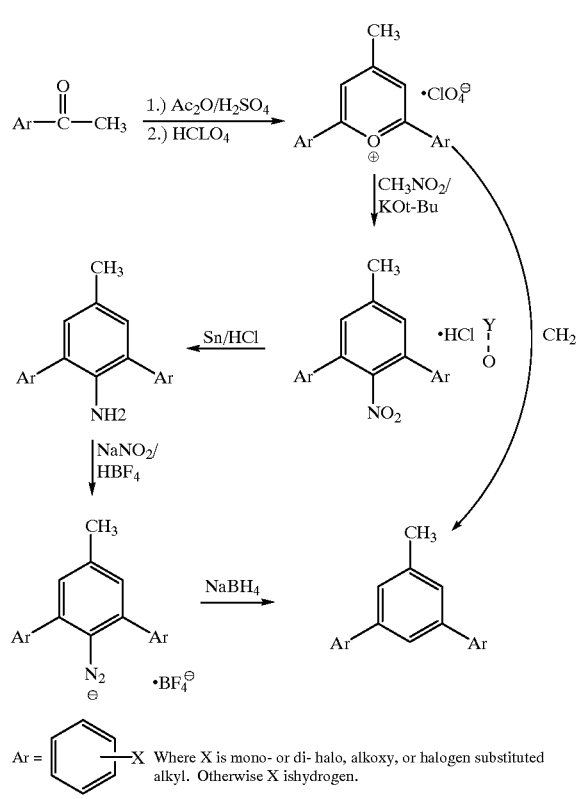

Preparing starting materials:

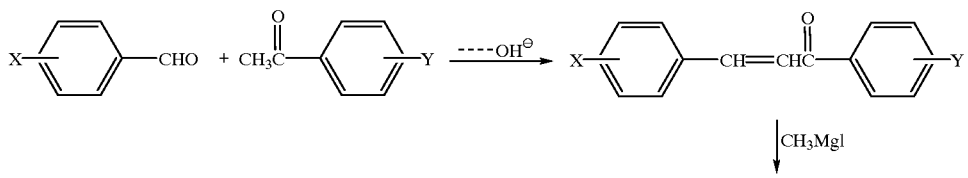

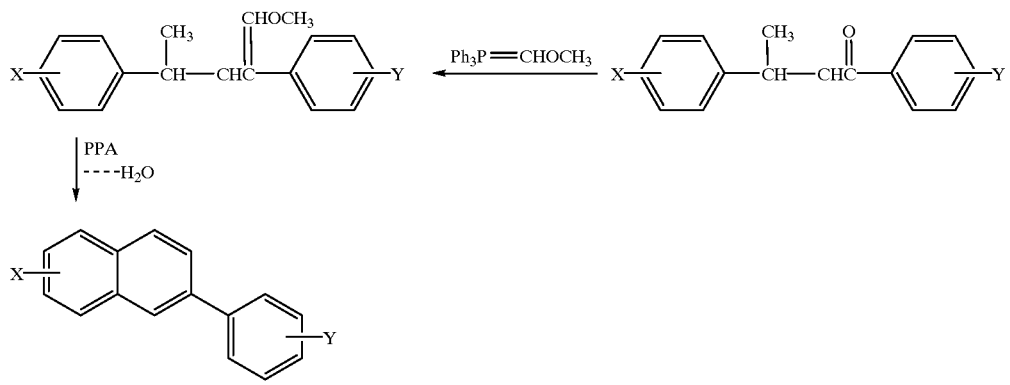
A general method for production:
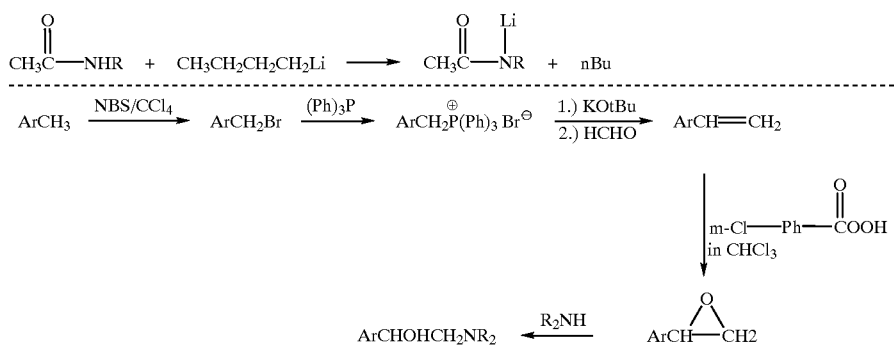
Side Chain Introductions
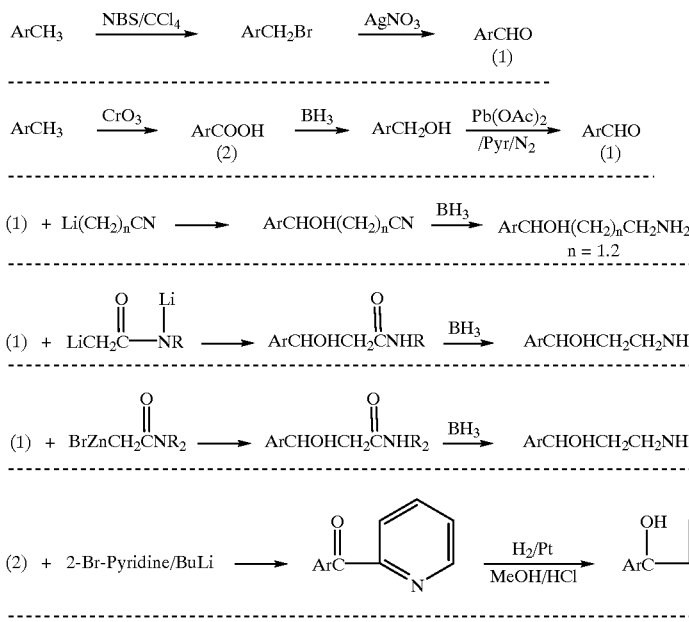

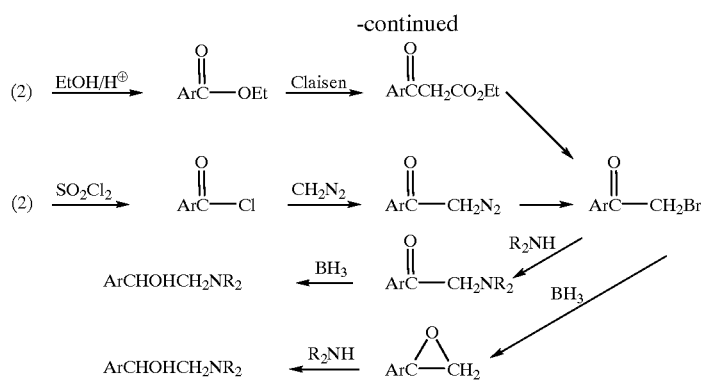

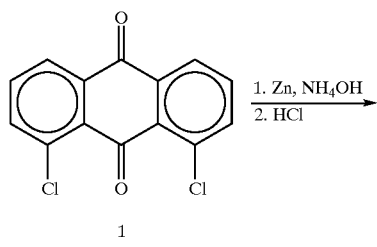

a-(2-PIPERIDYL)-4,5-DICHLORO-9-ANTHRACENEMETHANOL
(WR 218394)

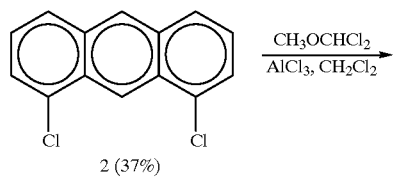

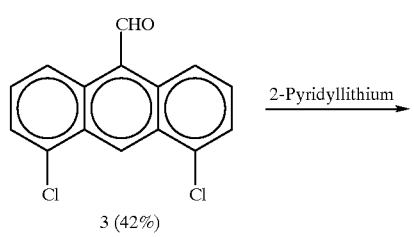

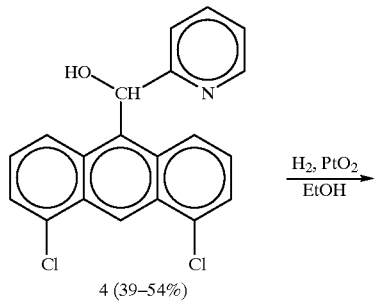

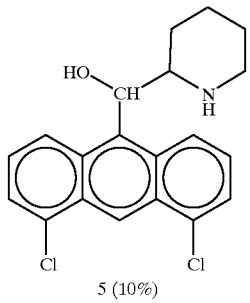

5 (10%)

Compounds of the general formula wherein A is a phenanthrene ring are known. Compounds are of the following formula:

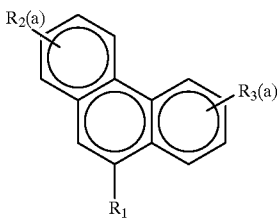

Formula IV wherein $R_1$ is a carbon bound directly to an oxygen and is also bound to a nitrogen through a saturated carbon and is of the structure CHOZX wherein Z may be hydrogen, a second bond to the oxygen, or may be carboxyl, ether or ester moiety wherein the ether or ester moiety may be alkyl of 1–8 carbons, phenyl, phenylalkyl, wherein the alkyl moiety consists of 1–4 carbons and wherein any said alkyl or phenyl group may, additionally, be substituted with hydroxy, alkyl of 1–2 carbons, alkenyl of 2–3 carbons, halo, amino, or alkyl amino group, X is $(CH_2)N((CH2)_n(CH_3))_m$ wherein is 1–3, n is $\leq 6$, m is 1 or 2 with the proviso that when m is 2, at least one n is <3, or X may be $(CH_2)_oJ$ as defined in the general formula, wherein $R_2$ and $R_3$ are as defined in the general formula and a is 0 to 3, with the proviso that for at least one of $R_2$ or $R_3$ a is 1–3. Preferred halo substituents are chloro or bromo and preferred haloalkyl is trifluoromethyl. A particularly useful member of this group of compounds is desbutylhalofantrine. which has now been found to be superior to halofantrine for treatment of malaria. (See U.S. Pat. No. 5,711,966, which is incorporated herein by reference in its entirety.)

The phenanthrenes may be made by several methods, including the following scheme:

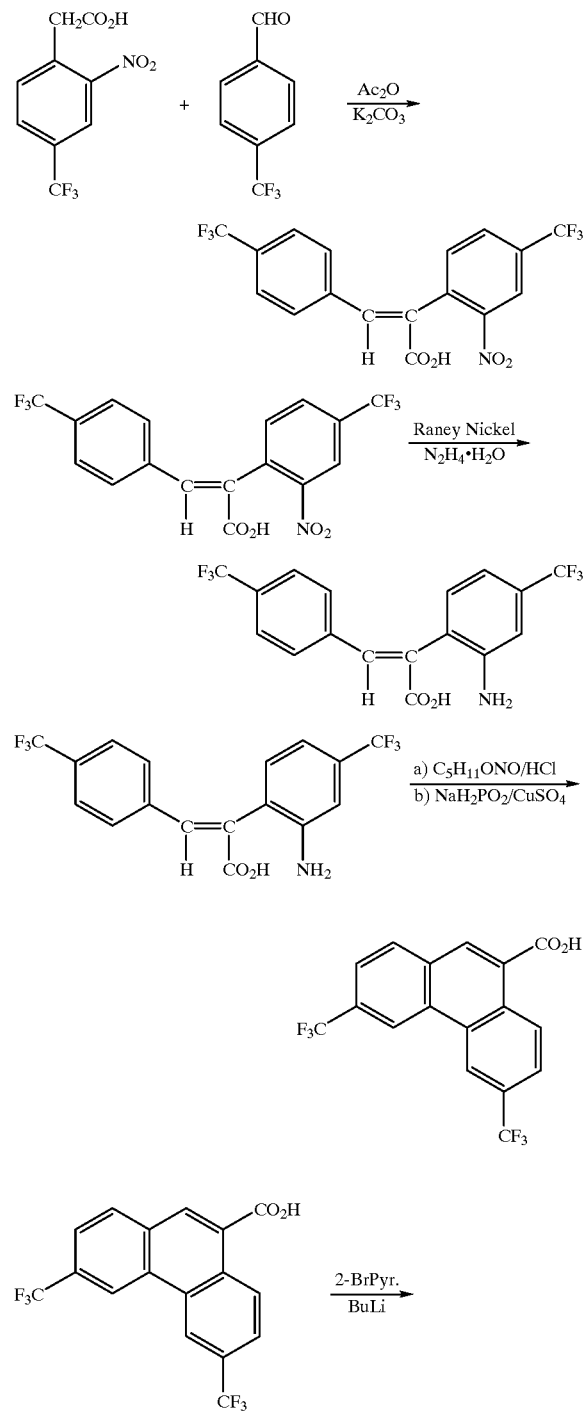

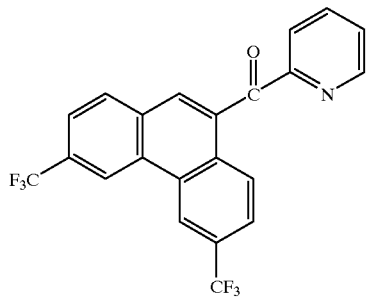

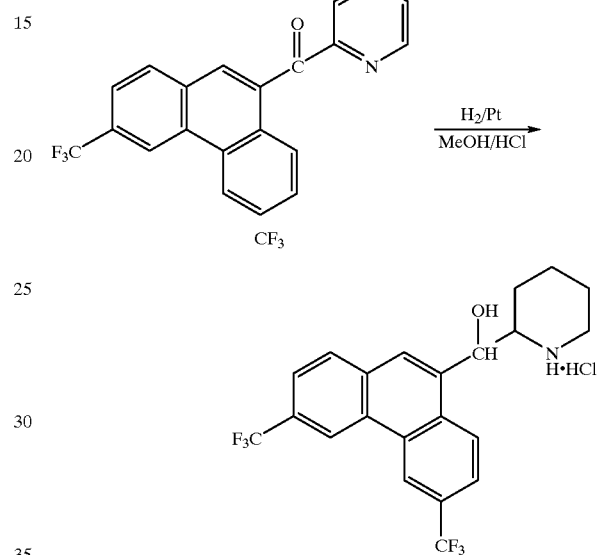

The phenanthrene compounds may also be prepared using the phenanthroic acid chlorides.

EXAMPLE 1

To a solution of 2 g of 10-(ω-bromoacetyl) -2,7-dichlorophenanthrene in 25 ml of THF is added 2.9 g. of di-n-heptylamine in 5 ml of THF at ambient temperature. After one hour, the THF is evaporated, the residue triturated with pentane, and filtered. The pentane residue is dissolved in EtOH/THF and reacted with 0.42 g of $NaBH_4$ for 1.5 hours. The resulting reaction mixture is concentrated, the diluted with $H_2H$, extracted with $Et_2O$, and acidified with gaseous HCl to yield the dichlorophenanthraceneaminoalcohol HCl salt.

Several active agents of the invention were tested for activity against several infectious organisms. Some of the methods used in testing are described below.

Media:

The strains were streaked on blood agar plates (trypticase soy broth containing 5% sheep cells). A single colony was isolated and grown in Mueller-Hinton Broth (MHB) as recommended by the national Committee for Clinical Laboratory Standards for rapidly growing bacteria. Candida species and related yeasts were isolated in a similar manner on brain-heart infusion agar (BHI).

Susceptibility tests:

The antibiotic susceptibility profile of each strain was determined using standard microtiter dilution plates obtained from the Clinical Microbiology Laboratory at Ohio State University Hospitals. The Inocula were prepared by suspending a 4 hour log phase growth in MHB visually equal in turbidity of an 0.5 McFarland standard. Inocula were further diluted and added to microdilution trays to achieve a final density of approximately $1 \times 10^5$ CFU/ml. The trays were incubated for 16 to 20 hours at 35° C. The highest dilution at which wells remained clear was considered to be the minimum inhibitory concentration (MIC).

The MIC and minimum bacterial concentration (MBC) of the strains to the active agents were determined by two-fold dilutions in Mueller-Hinton broth. Susceptibility tests for ATCC-obtained microorganisms and clinical isolates of gram positive bacteria including methicillin-susceptible and resistant staphylococci, streptococci, pneumococci and gram negative bacteria, including Enterobacteriaceae, Pseudomonas, Hemophilus and Neisseria, were performed in microtiter plates as described above.

Compounds of the invention were dissolved in 1 ml of methanol and stored in aliquots at −70° C. They were diluted in Mueller-Hinton broth for final screening. Compositions were tested in 0.1 ml volumes by serial dilution in microtiter plates against *Staphylococcus aureus* methicillin-sensitive ATCC 29213 and the methicillin-resistant wild type T67738, as described above. The T67738 was resistant to most antimicrobial drugs, including ciprofloxacin.

The most active compounds were studied further by time and dose-related killing curve analysis using large inocula ($1 \times 10^7$ CFU/ml).

The dosage and method of administration will depend on the location of the infection, the condition of the patient and the availability of professional supervision. Methods of administration include parenteral, oral, buccal, nasal or endotracheal routes. The active agents may be administered as sprays. For nasal administration, the active agent may be delivered as a powder that is snorted. Inclusion complexes such as cyclodextrin inclusion complexes would be particularly useful for buccal administration of these active agents.

The compounds of the invention may also be administered topically by any means, including by rectal route. Suppositories, solutions for use as retention enemas, and creams or jellies are appropriate carriers for use in rectal administration. The agents may be administered directly to infected tissue. For example, in case of open wounds, the active agents may be administered in the form of sprays or ointments.

Compounds of the invention may be applied to the skin or mucosa, including the vaginal mucosa, using creams, jellies, suppositories, or solutions. The active agents of the invention may be delivered directly to the epithelial tissue topically. For example, during surgery compositions containing the active agents of the invention to the applied directly to target tissues and prosthetic devices. The compositions could be given by aerosol into the trachea or administered in mist along with other agents into the respiratory tract.

The compositions of the invention may also be used prophylactically to protect from infection by pathogenic organisms.

Dosage forms containing about 25 to 1000 mg for administration by mouth are suggested for use in adults. However, because the condition and size of the patient and the infecting organisms may differ greatly, eventual dosage requirements must be adjusted by the physician. Hence, dosage suggestions are provided to give general guidance to those of skill in the art. In accord with the purposes of providing such guidance, the following data is provided.

The concentration required to provide benefit was studied in culture and provides guidance for effective concentration in the blood of the infected animal. The results of these studies may be seen in Tables I and II

TABLE I

| Active agent:<br>$R_1$ CHOZX | other substitutions: | Effective Concentration<br>*S. Aureous* (Resist). |
|---|---|---|
| Formula I<br>Z = H, X = $CH_2$-(2-piperidinyl)<br>(WR 218394) | $R_2$ and $R_4$ are Cl | 3.1 µg/ml |
| Formula II<br>Z = H, X = $CH_2$-(2-piperidinyl)<br>(WR 184366)<br>(the acetate) | $R_6$ = Cl, $R_7$ = $OCH_3$,<br>$R_3$ = 4-Cl-phenyl | 3.13 µg/ml |
| Z = H, X = $CH_2$-(2-piperidinyl)<br>(WR 185308)<br>(the acetate) | $R_6$ = Cl, $R_7$ = $OCH_3$,<br>$R_3$ = 3,4 dichloro-phenyl | 6.25 µg/ml |

The above compounds are also important for use
in treatment of mycobacterial and fungal infections.
Other compounds include those of the formula:

Formula I

| | | |
|---|---|---|
| $R_1$ is CHOZX and Z = H, X = $CH_2$—$N(C_4H_9)(C_3H_7)$ | $R_5$ and $R_6$ are Cl | (WR 201674) |
| $R_1$ is CHOZX and Z = H, X = $(CH_2)_2NHC_3H_7$ | $R_3$ is Cl | (WR 198118) |
| $R_1$ is CHOZX and Z = H, X = $(CH_2)_2NHC_3H_7$ | $R_3$ is Cl, $R_5$ is $CF_3$ | (WR 201683) |

-continued

The above compounds are also important for use
in treatment of mycobacterial and fungal infections.
Other compounds include those of the formula:

Formula II

Z = H, X = CH$_2$-(2-piperidinyl)    R$_6$ = Cl, R$_7$ = CF$_3$, R$_3$ = 4-Cl-phenyl
Z = H, X = CH$_2$-(2-piperidinyl)    R$_6$ = CF$_3$, R$_7$ = OCH$_3$, R$_3$ = 3,4 dichloro-phenyl Formula III Z = H, X = CH$_2$-(2-piperidinyl)        R$_3$ and R$_5$ are 4-Cl-phenyl
Z = H, X = CH$_2$- (2-piperidinyl)       R$_3$ = Cl, R$_5$ = 4-OCH$_3$-phenyl
Z = H, X = CH$_2$CH$_2$(2-piperidinyl)  R$_3$ = Cl, R$_5$ = 4-OCH$_3$-phenyl Formula IV

| Active agent: | | | | | | Effective Concentration *S. Aureous* |
|---|---|---|---|---|---|---|
| Z | X | R$_2$, | n | R$_3$ | n | Sens. Resist. Mycobacteria |
| H | piperidinyl (#1) | CF$_3$ | 1 | CF$_3$ | 1 | 1.56 |
| H | piperidinyl (#2) | Cl | 1 | CF$_3$ | 1 | 3.3 |
| H | piperidinyl (#3) | Cl | 2 | CF$_3$ | 1 | 3.0 |
| H | piperidinyl (#4) | Br | 1 | Br | 1 | 1.5 |
| H | piperidinyl (#5) | Cl | 1 | Cl | 1 | .75 |
| H | CH$_2$-piperidinyl (#6) | Cl | 1 | Cl | 1 | 1.56 |
| H | piperidinyl (#7) | CF$_3$ | 2 | Cl | 2 | 3.0 |
| H | piperidinyl (#8) | CF$_3$ | 1 | CF$_3$ | 1 | 6.2 |
| H | CH$_2$-piperidinyl(#9) | Cl | 2 | CF$_3$ | 1 | 0.8 |
| H | CH$_2$NHCH(CH$_2$CH$_3$)$_2$ (#11) | CF$_3$ | 1 | CF$_3$ | 1 | 3.3 |
| H | (CH$_2$)NH(CH$_2$)$_3$CH$_3$ (#12) | CF$_3$ | 1 | Cl | 2 | 1.56 |

EXAMPLE 2

Capsules of a formulation of active agent designated #184366 for oral administration are prepared by containing 250 mg. of the active agent, 100 mg. starch, and 5 mg. magnesium stearate. The capsules are administered daily or twice a day to achieve a daily dosage of 500 mg. per day.

EXAMPLE 3

A preparation for application to the skin or mucosa may be prepared in the following manner:

| Ingredient | % w/w |
|---|---|
| Compound #185308 | 15.0% |
| glyceryl monostearate | 3.0% |
| Petrolatum | 83.5% |

EXAMPLE 4

A formulation for administration as a retention enema may be formulated in the following manner:

| Ingredient | w/w % |
|---|---|
| Compound #218394 | 15% |
| Propylene glycol | 85% |

When the active agent is administered to the mucosa of the oral cavity, it may be administered as a buccal tablet or spray for use in the oral-pharyngeal cavity and the nasal cavities.

EXAMPLE 5

To 15 ml of phosphate buffered saline is added 3 mg of compound #185308. The composition is placed in a bottle having a stopper with a smooth glass rod extending into the solution. The composition is applied to boils using the smooth glass rod as an applicator. The composition may also be administered as a spray from a bottle with an atomizer.

EXAMPLE 6

To a 4×4 inch bandage having a smooth surface on one side there is applied to the smooth surface 0.02 ml of the solution prepared as a 2 μM solution of active agent designated #183308 in PBS. The prepared bandage is then enclosed in a foil covering which is made air-tight. For application, the bandage is unwrapped and is applied smooth side down on the wound.

EXAMPLE 7

A composition is prepared for use on the skin or mucosa in the following manner:

| Ingredient | % w/w |
|---|---|
| Agent designated #201683 | 0.5% |
| propylene glycol | 13.0% |
| Phosphate buffered saline | 86.5% |

When the active agent is administered to the mucosa of the oral cavity, it may be administered as a buccal tablet or spray for use in the oral-pharyngeal cavity and the nasal cavities.

EXAMPLE 8

A composition prepared as a gel for application to the skin:

| Ingredient | % w/w |
|---|---|
| active agent #1843660 | 0.5% |
| propylene glycol | 10.0% |
| Polyethylene glycol | 89.5% |

EXAMPLE 9

A composition prepared for administration as a suppository:

| Ingredient | (% w/w) |
|---|---|
| Active agent #185308 | 0.5 mg |
| glyceryl monosterate | 1.0 Gm |
| hydrogenated coconut oil | 1.0 Gm |
| glyceryl monopalmitate | 1.0 Gm |

EXAMPLE 10

A composition for intravenous administration is prepared comprising:

| | |
|---|---|
| 184366 | 300 mg. |
| 10% glucose in ½ normal saline | to 300 ml. |

Regarding the compounds of Formula IV (Phenanthrenes), the following examples are provided:

EXAMPLE 11

Capsules of a formulation of active agent designated #1 for oral administration are prepared by containing 250 mg. of the active agent, 100 mg. starch, and 5 mg. magnesium stearate. The capsules are administered daily or twice a day to achieve a daily dosage of 500 mg. per day.

EXAMPLE 12

A preparation for application to the skin or mucosa may be prepared in the following manner:

| Ingredient | % w/w |
|---|---|
| Compound #3 | 15.0% |
| glyceryl monostearate | 3.0% |
| Petrolatum | 83.5% |

EXAMPLE 13

A formulation for administration as a retention enema may be formulated in the following manner:

| Ingredient | % w/w |
|---|---|
| Compound #10 | 15% |
| Propylene glycol | 85% |

When the active agent is administered to the mucosa of the oral cavity, it may be administered as a buccal tablet or spray for use in the oral-pharyngeal cavity and the nasal cavities.

EXAMPLE 14

To 15 ml of phosphate buffered saline is added 3 mg of compound #11. The composition is placed in a bottle having a stopper with a smooth glass rod extending into the solution. The composition is applied to boils using the smooth glass rod as an applicator. The composition may also be administered as a spray from a bottle with an atomizer.

EXAMPLE 15

To a 4×4 inch bandage having a smooth surface on one side there is applied to the smooth surface 0.02 ml of the solution prepared as a 2 $\mu$M solution of active agent designated #4 in PBS. The prepared bandage is then enclosed in a foil covering which is made air-tight. For application, the bandage is unwrapped and is applied smooth side down on the wound.

EXAMPLE 16

A composition is prepared for use on the skin or mucosa in the following manner:

| Ingredient | % w/w |
|---|---|
| Agent designated #9 | 0.5% |
| propylene glycol | 13.0% |
| Phosphate buffered saline | 86.5% |

When the active agent is administered to the mucosa of the oral cavity, it may be administered as a buccal tablet or spray for use in the oral-pharyngeal cavity and the nasal cavities.

EXAMPLE 17

A composition prepared as a gel for application to the skin:

| Ingredient | % w/w |
|---|---|
| active agent designated #3 | 0.5% |
| propylene glycol | 10.0% |
| Polyethylene glycol | 89.5% |

EXAMPLE 18

A composition prepared for administration as a suppository:

| Ingredient | (% w/w) |
|---|---|
| Active agent #8 | 0.5 mg |
| glyceryl monosterate | 1.0 Gm |
| hydrogenated coconut oil | 1.0 Gm |
| glyceryl monopalmitate | 1.0 Gm |

EXAMPLE 19

A composition for intravenous administration is prepared comprising:

| | |
|---|---|
| Desbutylhalofantrine: | 300 mg. |
| 10% glucose in ½ normal saline | to 300 ml. |

The compositions for intravenous administration are particularly valuable for administration intravenously during heart surgery and to patients suffering from endocarditis.

What we claim is:

1. A method of treating or preventing infection caused by bacteria, mycobactera or fungi by administration of a composition containing as an active agent a bacteria, mycobacteria or yeast growth-inhibiting effective amount of a compound of the formula:

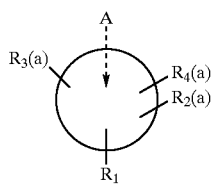

wherein A is a phenanthrene ring system, $R_1$ is bound directly to an oxygen and is also bound to a nitrogen through a saturated carbon or carbon chain, and $R_1$ is CHOZX wherein Z may be hydrogen, a second bond to the oxygen, or may be ether or ester moiety wherein the ether or ester moiety may be alkyl of 1–8 carbons, phenyl, phenylalkyl, wherein the alkyl moiety consists of 1–4 carbons and wherein any said alkyl or phenyl group may, additionally, be substituted with hydroxy, alkyl of 1–2 carbons, alkenyl of 2–3 carbons, halo, amino, or alkyl amino group and X is $(CH_2)N((CH2)_n(CH_3))_m$ wherein is 1 to 3, n is $\leq 6$, m is 1 or 2 with the proviso that when m is 2, at least one of n is <3, or X may be $(CH_2)_oJ$ wherein o is 0–4 and J is a saturated nitrogen-containing ring system with up to 10 carbon atoms in the ring system and may have up to 4 bridge carbons, and wherein any saturated ring system may be substituted with alkyl, alkenyl, halo, alkoxy or haloalkyl moieties of 1–5 carbons or with phenyl, phenoxy, phenylalkyl, phenylalkoxy, carboxy or carbonyl groups, wherein the carboxy or carbonyl groups, including keto or ester moieties, with alkyl groups having 1–4 carbons, alkenyl groups of 2–5 carbons or phenylalkyl wherein the alkyl is of 1–3 carbons or phenylalkoxy wherein the alkyl is of 1–3 carbons and, further, wherein X and Z may be linked to form a heterocyclic ring system and (a) is 0–4 with the proviso that at least one of (a) is not 0, $R_2$, $R_3$ and $R_4$ may be alkyl (including cycloalkyl), a saturated, nitrogen-containing ring of 4–10 atoms, alkoxy, aryl, aryloxy, aryloxyalkyl, amino, amino-alkyl, alkyl-aminoalkyl, arylamino, alkenyl, arylalkenyl, arylalkylaminoalkyl, carboxyalkyl, hydroxy, halo, alkenyl, or alkenyloxy, halo-substituted alkyl, wherein any alkyl has 1–8 carbons, alkenyl has 2–8 carbons, wherein halo is chloro, fluoro or bromo and aryl is a ring system of 1–3 rings and wherein any alkyl or aryl at $R_2$, $R_3$ and $R_4$ may be further substituted with halo (including multiple halo subtitutions), aryl of 1–2 rings, alkyl, haloalkyl or alkoxy, with the proviso that at least one of $R_2$, $R_3$ and $R_4$ is an electron-rich substituent.

2. A method of claim 1 of treating or preventing infection caused by bacteria, mycobacteria or fungi by administration of a composition containing as an active agent a bacteria, mycobacteria or yeast growth-inhibiting effective amount of a compound of the formula:

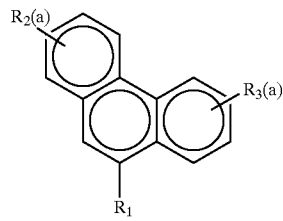

wherein any (a) is 1–3 and $R_2$, and $R_3$, may be H, alkyl (including cycloalkyl), a saturated, nitrogen-containing ring of 4–10 atoms, alkoxy, aryl, aryloxy, aryloxyalkyl, amino, amino-alkyl, alkyl-aminoalkyl, arylamino, alkenyl, arylalkenyl, arylalkylaminoalkyl, carboxyalkyl, hydroxy, halo, alkenyl, or alkenyloxy, halo-substituted alkyl, wherein any alkyl has 1–8 carbons, alkenyl has 2–8 carbons, wherein halo is chloro, fluoro or bromo and aryl is a ring system of 1–3 rings and wherein any alkyl or aryl may be further substituted with halo (including multiple halo substitutions), aryl of 1–2 rings, alkyl, haloalkyl or alkoxy, with the proviso that at least one of $R_2$ and $R_3$ is an electron-rich substituent and $R_1$ is the structure CHOZX wherein Z may be hydrogen, a second bond to the oxygen, or may be carboxyl, ether or ester moiety wherein the ether or ester moiety may be alkyl of 1–8 carbons, phenyl, phenylalkyl, wherein the alkyl moiety consists of 1–4 carbons and wherein any said alkyl or phenyl group may, additionally, be substituted with hydroxy, alkyl of 1–2 carbons, alkenyl of 2–3 carbons, halo, amino, or alkyl amino group and X is $(CH_2)_lN((CH2)_n(CH_3))_m$ wherein $l$ is 1–3, n is $\leq 6$, m is 1 or 2 with the proviso that when m is 2, at least one n is <3, or X may be $(CH_2)_oJ$ wherein o is 0–4 and J is a saturated nitrogen-containing ring system with up to 10 carbon atoms in the ring system and way have up to 4 bridge carbons, and wherein any saturated ring system may be substituted with alkyl, alkenyl, halo, alkoxy or haloalkyl moieties of 1–5 carbons or with phenyl, phenoxy, phenylalkyl, phbnylalkoxy, carboxy or carbonyl groups, wherein the carboxy or carbonyl groups, including keto or ester moieties, with alkyl groups having 1–4 carbons, alkenyl groups of 2–5 carbons or phenylalkyl wherein the alkyl is of 1–3 carbons or phenylalkoxy wherein the alkyl is of 1–3 carbons, and, furthermore, X and Z may be linked to form a heterocyclic ring system.

3. A method of claim 1 wherein the active agent is desbutylhalofantrine.

4. A method of claim 1 wherein the active agent is chosen from among compounds wherein substitutents are:

| Z | X | $R_2$, | n | $R_3$ | n |
|---|---|---|---|---|---|
| H | piperidinyl (#1) | $CF_3$ | 1 | $CF_3$ | 1 |
| H | piperidinyl (#2) | Cl | 1 | $CF_3$ | 1 |
| H | piperidinyl (#3) | Cl | 2 | $CF_3$ | 1 |
| H | piperidinyl (#4) | Br | 1 | Br | 1 |
| H | piperidinyl (#5) | Cl | 1 | Cl | 1 |
| H | $CH_2$-piperidinyl (#6) | Cl | 1 | Cl | 1 |
| H | piperidinyl (#7) | $CF_3$ | 2 | Cl | 2 |
| H | piperidinyl (#8) | $CF_3$ | 1 | $CF_3$ | 1 |
| H | $CH_2$-piperidinyl (#9) | Cl | 2 | $CF_3$ | 1 |

-continued

| Z | X | $R_2$, | n | $R_3$ | n |
|---|---|---|---|---|---|
| H | $CH_2NHCH(CH_2CH_3)_2$ (#11) | $CF_3$ | 1 | $CF_3$ | 1 |
| H | $(CH_2)NH(CH_2)_3CH_3$ (#12) | $CF_3$ | 1 | Cl | 2. |

5. A compound of the formula:

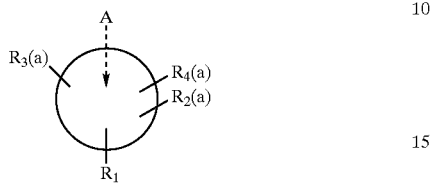

wherein A is a phenanthrene ring system, $R_1$ is bound directly to an oxygen and is also bound to a nitrogen through a saturated carbon or carbon chain, wherein $R_1$ is CHOZX wherein Z may be hydrogen, a second bond to the oxygen, or may be carboxyl, ether or ester moiety wherein the ether or ester moiety may be alkyl of 1–8 carbons, phenyl, phenyl-alkyl, wherein the alkyl moiety consists of 1–4 carbons and wherein any said alkyl or phenyl group may, additionally, be substituted with hydroxy, alkyl of 1–2 carbons, alkenyl of 2–3 carbons, halo, amino, or alkyl amino group and X is $(CH_2)_oJ$ wherein o is 2–4 and J is a saturated nitrogen-containing ring system with up to 10 carbon atoms in the ring system and may have up to 4 bridge carbons, and wherein any saturated ring system may be substituted with alkyl, alkenyl, halo, alkoxy or haloalkyl moieties of 1–5 carbons or with phenyl, phenoxy, phenylalkyl, phenylalkoxy, carboxy or carbonyl groups, wherein the carboxy or carbonyl groups, including keto or ester moieties, with alkyl groups having 1–4 carbons, alkenyl groups of 2–5 carbons or phenylalkyl wherein the alkyl is of 1–3 carbons or phenylalkoxy wherein the alkyl is of 1–3 carbons, and (a) is 0–4 with the proviso that at least one of (a) is not 0, $R_2$, $R_3$ and $R_4$ may be alkyl (including cycloalkyl), a saturated, nitrogen-containing ring of 4–10 atoms, alkoxy, aryl, aryloxy, aryloxyalkyl, amino, aminoalkyl, alkyl-aminoalkyl, arylamino, alkenyl, arylalkenyl, aryl- alkylaminoalkyl, carboxyalkyl, hydroxy, halo, alkenyl, or alkenyloxy, halo-substituted alkyl, wherein any alkyl has 1–8 carbons, alkenyl has 2–8 carbons, wherein halo is chloro, fluoro or bromo and aryl is a ring system of 1–3 rings and wherein any alkyl or aryl at $R_2$, $R_3$ and $R_4$ may be further substituted with halo (including multiple halo substitutions), aryl of 1–2 rings, alkyl, haloalkyl or alkoxy, with the proviso that at least one of $R_2$, $R_3$ and $R_4$ is an electron-rich substituent.

* * * * *